US012806132B2

(12) United States Patent
Yamazaki

(10) Patent No.: US 12,806,132 B2
(45) Date of Patent: Nov. 24, 2026

(54) HAIR COSMETIC

(71) Applicant: KAO CORPORATION, Tokyo (JP)

(72) Inventor: Naoyuki Yamazaki, Sumida-ku (JP)

(73) Assignee: KAO CORPORATION, Tokyo (JP)

(*) Notice: Subject to any disclaimer, the term of this patent is extended or adjusted under 35 U.S.C. 154(b) by 413 days.

(21) Appl. No.: 18/557,831

(22) PCT Filed: Apr. 28, 2022

(86) PCT No.: PCT/JP2022/019323
§ 371 (c)(1),
(2) Date: Oct. 27, 2023

(87) PCT Pub. No.: WO2022/230985
PCT Pub. Date: Nov. 3, 2022

(65) Prior Publication Data
US 2024/0216258 A1 Jul. 4, 2024

(30) Foreign Application Priority Data
Apr. 30, 2021 (JP) ................................ 2021-077877

(51) Int. Cl.

| | |
|---|---|
| ***C11D 1/02*** | (2006.01) |
| ***A61K 8/46*** | (2006.01) |
| ***A61K 8/73*** | (2006.01) |
| ***A61K 8/81*** | (2006.01) |
| ***A61K 8/92*** | (2006.01) |

(Continued)

(52) U.S. Cl.
CPC ............ *A61K 8/8147* (2013.01); *A61K 8/466* (2013.01); *A61K 8/731* (2013.01); *A61K 8/92* (2013.01); *A61Q 5/08* (2013.01); *A61Q 5/12* (2013.01)

(58) Field of Classification Search
CPC ....... C11D 1/02; C11D 3/3715; C11D 3/3746; C11D 3/3749; C11D 3/3757; C11D 3/3769; C11D 3/3796; A61K 8/466; A61K 8/731; A61K 8/81; A61K 8/8147; A61Q 5/02; A61Q 5/12
See application file for complete search history.

(56) References Cited

U.S. PATENT DOCUMENTS

| | | | |
|---|---|---|---|
| 2009/0286707 | A1 | 11/2009 | Uchiyama et al. |
| 2019/0105244 | A1 | 4/2019 | Song et al. |
| 2020/0397680 | A1 | 12/2020 | Yoshida et al. |

FOREIGN PATENT DOCUMENTS

| | | | |
|---|---|---|---|
| CN | 111686049 A | 9/2020 | |
| CN | 111956587 A * | 11/2020 | ............... A61K 8/98 |

(Continued)

OTHER PUBLICATIONS

Japanese Office Action issued Sep. 17, 2024 in Japanese Patent Application No. 2022-075415, 5 pages (with machine English translation).

(Continued)

*Primary Examiner* — Brian P Mruk
(74) *Attorney, Agent, or Firm* — Oblon, McClelland, Maier & Neustadt, L.L.P.

(57) ABSTRACT

A hair cosmetic containing the following components (A) to (D): (A) an anionic polymer, (B) an anionic surfactant, (C) a cationic polymer having a cellulose backbone, and (D) a cross-linked cationic vinyl polymer. A hair treatment method including applying the hair cosmetic to a hair and rinsing the hair in which the hair cosmetic is applied with water.

20 Claims, 1 Drawing Sheet

(a)

(b)

(51) Int. Cl.

| | |
|---|---|
| ***A61Q 5/02*** | (2006.01) |
| ***A61Q 5/08*** | (2006.01) |
| ***A61Q 5/12*** | (2006.01) |

(56) References Cited

FOREIGN PATENT DOCUMENTS

| | | | |
|---|---|---|---|
| CN | 111700843 | B | 3/2021 |
| JP | 2017-88516 | A | 5/2017 |
| JP | 2017-137254 | A | 8/2017 |
| JP | 2017-210413 | A | 11/2017 |
| JP | 2017-210417 | A | 11/2017 |
| JP | 2019-94326 | A | 6/2019 |
| JP | 2020-536959 | A | 12/2020 |
| WO | WO 2020/025275 | A1 | 2/2020 |

OTHER PUBLICATIONS

International Search Report issued Jul. 19, 2022 in PCT/JP2022/019323 (with English translation), 5 pages.
Written Opinion of the International Searching Authority issued Jul. 19, 2022 in PCT/JP2022/019323 (with English translation), 6 pages.
Extended European Search Report issued Mar. 25, 2025, in corresponding European Patent Application No. 22795898.0, 16 pages.
Anonymous: "Moisture Cream Conditioner Nourishing Formula", XP055981344, Database accession No. 404208, Database GNPD [Online] MINTEL; Oct. 10, 2005, 2 pages.

* cited by examiner

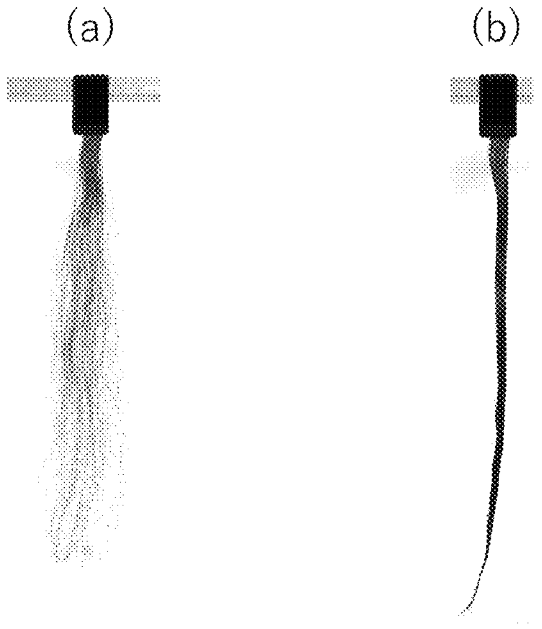
(a)
(b)

HAIR COSMETIC

CROSS REFERENCE TO RELATED APPLICATIONS

This application is a National Stage entry under 35 U.S.C. § 371 of PCT/JP2022/019323, filed on Apr. 28, 2022, and claims priority to Japanese Patent Application No. 2021-077877, filed on Apr. 30, 2021. The entire contents of both are incorporated herein by reference.

FIELD OF THE INVENTION

The present invention relates to a hair cosmetic and a hair treatment method.

BACKGROUND OF THE INVENTION

In recent years, hair cosmetics are increasingly expected to have a conditioning effect that can impart smoothness, softness, manageability and the like to the hair. There have been already reported the techniques for imparting smoothness, softness, manageability and the like to the hair by blending a cationic polymer and an anionic polymer.

For example, JP2017-210413A (PTL 1) describes that a hair treatment agent containing (A) cationic polysaccharides, (B) a specific cross-linked cationic polymer, (C) a fatty acid or a salt thereof, and (D) a cationic surfactant, can make the hair less prone to get the bed hair, impart the smoothness to the hair while suppressing the stickiness when rinsing, and keep the manageability and smoothness of the hair until the next washing.

JP2017-88516A (PTL 2) describes that a hair detergent composition containing (A) an anionic surfactant, (B) a cross-linked cationic polymer, a hydrophobic cationised hydroxyethylcellulose and water, can make the hair excellent to the ease of separation, little entangled, little squeakiness, rich feelings when rinsing, and further, can dry the wet hair after washing in a short time.

JP2017-137254A (PTL 3) describes that a hair detergent composition containing a component (A): an anionic surfactant, a component (B): a cationic polymer, a component (C): a polymer containing a specific configuration unit, and water, in which a mass ratio ((B)/(C)) of the content of the component (B) with respect to the content of the component (C) in the hair detergent composition is in a specific range, can make the hair less prone to get the bed hair, and can impart the manageability and preferable smoothness and softness to the hair while touching.

SUMMARY OF THE INVENTION

The present invention relates to a hair cosmetic which improved a shape fixing ability of the hair, and a hair treatment method.

The hair cosmetics in recent years are endowed with new functions such as suppressing the curls of the hair and then imparting the manageability of the hair, but a technique for controlling the shape of the hair itself has not been established. Therefore, there is a demand for functions of fixing the shape while imparting a certain shape by bundling the hair, for example, a function of fixing the peculiar hair such as curly hair into a straight shape, or fixing into a clumped wavy shape by bunding. The hair cosmetics described in the above PTL 1 to 3 had a room for improvement in terms of the shape fixing ability of the hair.

The present inventor found that the hair cosmetic containing (A) an anionic polymer, (B) an anionic surfactant, (C) a cationic polymer having a cellulose backbone, and (D) a cross-linked cationic vinyl polymer, can improve the shape fixing ability of the hair, and completed the present invention.

Specifically, the present invention relates to the following items [1] and [2].

[1] A hair cosmetic containing the following components (A) to (D):

(A) an anionic polymer;

(B) an anionic surfactant;

(C) a cationic polymer having a cellulose backbone; and (D) a cross-linked cationic vinyl polymer.

[2] A hair treatment method containing:

a step of applying the hair cosmetic according to the above item [1]; and a step of rinsing the hair in which the hair cosmetic is applied, with water.

According to the present invention, it is possible to provide the hair cosmetic which improved the shape fixing ability of the hair, and the hair treatment method.

BRIEF DESCRIPTION OF THE DRAWING

FIG. 1 is a diagram for explaining the shape fixing of the hair, and illustrates a photograph of the state in which the upper end of the hair bundle is fixed and hung, viewed from the front. In the figure, (a) shows the untreated hair bundle for the evaluation, and (b) shows the state in which the untreated hair bundle for the evaluation of (a) was treated with the hair cosmetic of the present invention and controlled into straight shape by a ring comb, and completely dried with a dryer.

[Hair Cosmetic]

The hair cosmetic of the present invention contains the following components (A) to (D).

(A) an anionic polymer (B) an anionic surfactant (C) a cationic polymer having a cellulose backbone (D) a cross-linked cationic vinyl polymer Note that, in the present invention, "to contain a component X" shall be regarded as having the same meaning as "to be formed by mixing a component X".

According to the hair cosmetic of the present invention, it is possible to improve the shape fixing ability for fixing the shape of the bundled hair while imparting a certain shape by bundling the hair. Therefore, particularly when styling the peculiar hair such as curly hair, into a straight shape or a clumped wavy shape, it can reduce the time and the effort required, and can keep the formed shape in a long time, and can be suitably applicated.

FIG. 1 is a diagram for explaining the shape fixing of the hair, and illustrates a photograph of the state in which the upper end of the hair bundle is fixed and hung, viewed from the front. In the FIG. 1, (a) shows the untreated hair bundle for the evaluation, and (b) shows the state in which the untreated hair bundle for the evaluation of (a) was treated with the hair cosmetic of the present invention and controlled into straight shape by a ring comb, and completely dried with a dryer.

Specifically, in the present invention, "the shape fixing ability of the hair" means for example, the ability of strongly fixing the shape such that the shape is maintained even after drying, while bundling the peculiar hair as shown in the FIG. 1(*a*), and making it into a straight shape as shown in FIG. 1(*b*). Note that in the present invention, "shape fixing of the hair" means a state in which the hair is bound each other and the bundle of the hair is fixed in a specific shape, and is different from a state of "manageability of the hair" which means a state in which the hair line is beautiful and is not dishevelled from the top to the tip of hair.

For the reasons why the hair cosmetic of the present invention achieves the effects of the present invention due to the above configuration, it is presumed as follows.

The hair cosmetic of the present invention contains an anionic polymer as the component (A), an anionic surfactant as the component (B), a cationic polymer having a cellulose backbone as the component (C), and a cross-linked cationic vinyl polymer as the component (D).

It is possible to form a complex gel by interacting the component (A) which is an anionic polymer and the component (B) which is an anionic surfactant, with the component (C) and the component (D) which are cationic polymers.

Further, it is considered that when rinsing the hair to which the hair cosmetic of the present invention is applied, the excess component (B) which is the anionic surfactant is washed away, and the complex gel is deposited on the hair surface, and a complex gel film having a binding property is formed on the hair surface. It is considered that the hair in which the complex gel film having the binding property is formed, is bound each other and supported each other by the complex gel film, and the shape of the hair is fixed.

Here, since the component (C) is excellent in adhesion property to the hair, it is easily uniformly adsorbed to the entire hair, and the component (D) is excellent in water retention, and can increase the total amount of the formed complex gel. The action of both makes it possible to adsorb a large amount of gel to the hair. As described above, it is considered that since the hair cosmetic of the present invention can form a film having good binding ability uniformly on the entire hair by combining the components (A) to (D), it is possible to improve the shape fixing ability for fixing the shape of the bundled hair while imparting a certain shape by bundling the hair.

As embodiments of the hair cosmetic of the present invention, for example, hair cleansers such as a hair shampoo, a hair rinse, a hair conditioner, a hair treatment, a hair pack, a hair styling agent, and the like are given. Among these, the one that is used after washing the hair is preferable, and an embodiment that is used by rinsing after being applied to the hair is more preferable, from the viewpoint of further exhibiting the effect of the present invention. From this viewpoint, the hair cosmetic of the present invention is preferably a hair rinse, a hair conditioner, a hair treatment, a hair pack or a hair styling agent.

A formulation of the hair cosmetic of the present invention may be any formulation, for example, such as liquid, foam, paste or cream. Among these, liquid, paste or cream is preferable, and liquid is more preferable, from the viewpoint of ease of use.

<Component (A): Anionic Polymer>

The hair cosmetic of the present invention contains an anionic polymer as the component (A).

As the examples of the anionic polymer, for example, vinyl-based polymers having a carboxy group or a sulfonic acid group as an anionic group, are given. From the viewpoint of versatility, a vinyl-based polymer having a carboxy group is preferable. For example, vinyl-based polymers containing the structural units derived from crotonic acid, maleic acid, maleic acid monoester, itaconic acid, or (meth) acrylic acid, are given.

As the vinyl-based polymer having a carboxy group of the component (A), a polymer of acrylic acid is preferable. In addition, the content of the structural units derived from alkyl methacrylate in the vinyl-based polymer having a carboxy group of the component (A) is preferably 5% by mass or less, more preferably 1% by mass or less, still more preferably 0.5% by mass or less, still more preferably 0.1% by mass or less, and it is still more preferable that the vinyl-based polymer having a carboxyl group of the component (A) does not contain alkyl methacrylate as a constituent monomer. For this reason, in an aqueous medium, by the interaction with the component (C) and the component (D), the shape fixing ability of the hair can be further improved more than a polymer containing alkyl methacrylate, which is less hydrophilic than acrylic acid, as a monomer structural unit.

Further, the polymer of the component (A) is preferably a cross-linked type. When the component (A) is a cross-linked polymer, the effect of improving the water retention of the hair can be high, and the shape fixing ability of the hair can be further improved.

The component (A) preferably contains at least one selected from cross-linked polyacrylic acid and (acrylates/alkyl acrylate (C10-30)) crosspolymer, is more preferably at least one selected from cross-linked polyacrylic acid and (acrylates/alkyl acrylate (C10-30)) crosspolymer, and is still more preferably cross-linked polyacrylic acid, from the viewpoint of further improving the shape fixing ability of the hair.

As the cross-linked polyacrylic acid, carboxyvinyl polymers, that is, carbomer by the INCI name, are preferred. The carbomer is a polymer of acrylic acids crosslinked with pentaerystyl allyl ether, sucrose allyl ether or propylene allyl ether.

The component (A) is preferably a vinyl-based polymer having a carboxyl group as an anionic group, and forms a complex gel by the interaction with the component (C) and the component (D), which are cationic polymers having cationic properties. By the effect of improving the water retention of the hair and the effect of binding the hair each other by the complex gel, the shape fixing ability of the hair can be improved.

(Acrylates/alkyl acrylate (C10-30)) crosspolymer is the one in which a copolymer of one or more monomers composed of acrylic acid, methacrylic acid or their simple esters, and an alkyl acrylate (C10-30) are cross-linked with an allyl ether of sucrose or an allyl ether of pentaerythritol, and its INCI name is Acrylates/C10-30 Alkyl Acrylate Cross Polymer.

As the commercially available products of carbomers, for example, Carbopol (registered trademark; hereinafter abbreviated) 980, Carbopol 981 (manufactured by Lubrizol Corporation), and the like are given. As the commercially available products of the (acrylates/alkyl acrylate (C10-30)) cross polymer, Carbopol ETD2020 (manufactured by Lubrizol Corporation) and the like, are given.

The component (A) may be used alone or in combination of two or more.

The content of the component (A) in the hair cosmetic of the present invention is preferably 0.01% by mass or more, more preferably 0.03% by mass or more, still more preferably 0.05% by mass or more, still more preferably 0.08% by mass or more, still more preferably 0.10% by mass or more, still more preferably 0.20% by mass or more, from the viewpoint of further improving the shape fixing ability of the hair, and is preferably 5.0% by mass or less, more preferably 3.0% by mass or less, still more preferably 1.0% by mass or less, and still more preferably 0.80% by mass or less, from the same point of view. Taking these points together, the content of the component (A) in the hair cosmetic of the present invention is preferably 0.01% by mass or more and 5.0% by mass or less, more preferably 0.03% by mass or more and 3. 0% by mass or less, still more preferably 0.05% by mass or more and 1.0% by mass or less, still more preferably 0.08% by mass or more and 0.80% by mass or less, still more preferably 0.10% by mass or more and 0.80% by mass or less, and still more preferably 0.20% by mass or more and 0.80% by mass or less.

<Component (B): Anionic Surfactant>

The hair cosmetic of the present invention contains an anionic surfactant as the component (B).

The component (B) preferably contains at least one selected from the group consisting of polyoxyethylene alkyl ether sulfate and α-olefin sulfonate, more preferably contains polyoxyethylene alkyl ether sulfate, from the viewpoint of further improving the shape fixing ability of the hair.

As the polyoxyethylene alkyl ether sulfate, a compound represented by the following formula (I) is given.

$$R^1—O—(CH_2CH_2O)_p—SO_3Y \quad (I)$$

In the formula (I), $R^1$ represents a linear or branched alkyl group having 8 or more and 22 or less carbon atoms. p represents the average number of added moles and is a number of 0.25 or more and 20 or less. Y represents an alkali metal, an alkaline earth metal, ammonium, alkanolamine or basic amino acid.

The number of carbon atoms in the linear or branched alkyl group in $R^1$ is preferably 8 or more and 18 or less, more preferably 10 or more and 18 or less, from the viewpoint of further improving the shape fixing ability of the hair.

As the specific examples of $R^1$ in the formula (I), 2-ethylhexyl group, n-octyl group, nonyl group, n-decyl group, isodecyl group, undecyl group, n-dodecyl group, lauryl group, tridecyl group, myristyl group, pentadecyl group, palmityl group, heptadecyl group, stearyl group, isostearyl group, nonadecyl group, icosyl group, henicosyl group, and docosyl group are given. Among these, $R^1$ is preferably a linear alkyl group; more preferably one or more selected from the group consisting of n-octyl group, n-decyl group, lauryl group, myristyl group, cetyl group, and stearyl group; still more preferably one or more selected from the group consisting of n-decyl group, lauryl group, myristyl group, cetyl group and stearyl group; still more preferably lauryl group.

Furthermore, $R^1$ may be an alkyl group derived from multiple fatty acids contained in natural products such as coconut oil, palm oil, palm kernel oil, soybean oil, rapeseed oil, beef tallow, lard, or fish oil. In this case, the compound represented by the formula (I) is obtained as a mixture of a plurality of compounds having different alkyl groups.

p in the formula (I) represents the average number of added moles and is a number of 0.25 or more and 20 or less. p is preferably 0.5 or more, more preferably 1 or more and preferably 15 or less, more preferably 10 or less, and still more preferably 5 or less, from the viewpoint of further improving the shape fixing ability of the hair.

Y in the formula (I) represents an alkali metal, an alkaline earth metal, ammonium, alkanolamine or basic amino acid, preferably an alkali metal or ammonium.

As the alkali metal, lithium, sodium, or potassium is preferable. Ammonium may be alkylammonium or alkanolammonium.

Y is preferably one or more selected from the group consisting of sodium, potassium, and ammonium, more preferably one or more selected from the group consisting of sodium and ammonium, from the viewpoint of further improving the shape fixing ability of the hair.

As the specific examples of the polyoxyethylene alkyl ether sulfate represented by the formula (I), sodium laureth sulfate, ammonium laureth sulfate, and the like in which the average number of the added moles p of the oxyethylene group is 0.25 or more and 20 or less, preferably 0.5 or more and 15 or less, more preferably is 0.5 or more and 10 or less, still more preferably 1 or more and 5 or less, are given.

As the specific examples of sodium laureth sulfate, "EMAL 227HP" and "EMAL 125HP" manufactured by Kao Corporation, and the like are given, and as the specific examples of ammonium laureth sulfate, "EMAL 170S-A" manufactured by Kao Corporation and the like are given.

The number of carbon atoms in the α-olefin sulfonate is preferably 8 or more and 22 or less, more preferably 8 or more and 18 or less, and still more preferably 10 or more and 18 or less, from the viewpoint of further improving the shape fixing ability of the hair.

As the counter ion of the α-olefinsulfonic acid constituting the α-olefinsulfonate, alkali metal ions such as sodium ion and potassium ion; alkaline earth metal ions such as calcium ion and magnesium ion; ammonium ion; or alkanolammonium having 1 or more and 3 or less alkanol groups having 2 or 3 carbon atoms (for example, monoethanolammonium, diethanolammonium, triethanolammonium, triisopropanolammonium, and the like), are given.

The counter ion of the α-olefinsulfonic acid is preferably one or more selected from the group consisting of sodium, potassium and ammonium, more preferably sodium, from the viewpoint of further improving the shape fixing ability of the hair.

As the specific examples of α-olefin sulfonate, sodium sulfonates of α-olefins having preferably 8 or more and 22 or less carbon atoms, more preferably 10 or more and 18 or less carbon atoms.

As the anionic surfactants other than polyoxyethylene alkyl ether sulfates and α-olefin sulfonates, for example, alkylbenzene sulfonates, internal olefin sulfonates, alkyl or alkenyl sulfates, alkyl sulfonates, saturated or unsaturated fatty acid salts, alkyl or alkenyl ether carboxylates, α-sulfo fatty acid salts, N-acylamino acid salts, phosphoric acid mono or diester salts, sulfosuccinic acid ester salts, and the like, are given, and one or more of these can be used.

The hydrocarbon groups such as alkyl groups and alkenyl groups or the constituent fatty acids, which the anionic surfactants other than polyoxyethylene alkyl ether sulfates and α-olefin sulfonates has, preferably have 8 or more and 22 or less carbon atoms, more preferably have 8 or more and 18 or less carbon atoms, still more preferably 10 or more and 18 or less carbon atoms.

The internal olefin is an olefin having a double bond inside the olefin chain, and also contains the broad meaning of the case in which the position of the double bond is present at the 1-position of the carbon chain, that is, a slight amount of α-olefin is contained.

When the internal olefin is sulfonated, ß-sultones are quantitatively produced, and some of the ß-sultones are converted into γ-sultones and olefinsulfonic acids. Further, these are converted into hydroxyalkanesulfonates and internal olefinsulfonate by neutralization and hydrolysis steps. Here, the hydroxy group of the obtained hydroxyalkanesulfonate is inside the alkane chain and the double bond of the internal olefinsulfonate is inside the olefin chain.

The average double bond position of the internal olefin is preferably 3.0 or more, more preferably 3.5 or more, still more preferably 3.7 or more, and preferably 5.0 or less, more preferably 4.5 or less.

As the counter ion for the anionic group of the above anionic surfactant other than polyoxyethylene alkyl ether sulfate, alkali metal ions such as sodium ion and potassium ion; alkaline earth metal ions such as calcium ion and magnesium ion; ammonium ions; alkanolammonium having 1 or more and 3 or less alkanol groups having 2 or 3 carbon atoms (for example, monoethanolammonium, diethanolammonium, triethanolammonium, triisopropanolammonium, and the like), are given.

Among the above, as the anionic surfactant other than polyoxyethylene alkyl ether sulfate and α-olefin sulfonate, one or more selected from the group consisting of alkyl sulfates, internal olefin sulfonates, N-acylamino acid salts and alkyl ether carboxylates are preferable, from the viewpoint of further improving the shape fixing ability of the hair.

As the alkyl sulfate, sodium lauryl sulfate and the like are given. As the alkyl ether carboxylates, polyoxyethylene alkyl ether acetates such as sodium laureth acetate, are given. As the N-acylamino acid salts, cocoyl alanine salts and the like, are given.

The component (B) may be used alone or in combination of two or more.

The content of the component (B) in the hair cosmetic of the present invention is preferably 0.1% by mass or more, more preferably 0.2% by mass or more, still more preferably 0.3% by mass or more, still more preferably 0.4% by mass or more, still more preferably 0.5% by mass or more, from the viewpoint of further improving the shape fixing ability of the hair, and is preferably 20% by mass or less, more preferably 15% by mass or less, still more preferably 13% by mass or less, still more preferably 10% by mass or less, still more preferably 8.0% by mass or less, still more preferably 6.0% by mass or less, from the same viewpoint. Taking these points together, the content of the component (B) in the hair cosmetic of the present invention is preferably 0.1% by mass or more and 20% by mass or less, more preferably 0.2% by mass or more and 15% by mass or less, still more preferably 0.3% by mass or more and 13% by mass or less, still more preferably 0.4% by mass or more and 10% by mass or less, still more preferably 0.5% by mass or more and 8.0% by mass or less, still more preferably 0.5% by mass or more and 6.0% by mass or less.

<Component (C): Cationic Polymer Having a Cellulose Backbone>

The hair cosmetic of the present invention contains a cationic polymer having a cellulose backbone as the component (C).

In the present invention, "a cationic polymer having a cellulose backbone" means a polymer which has a cationic group and a cellulose backbone and has cationic charge as a whole. In addition, the cationic group means a cationic group, or a group which can be ionized to become a cationic group, for example, a quaternary ammonium group, or a tertiary amino group which can be converted to a tertiary amino group by adding a proton.

As the cationic polymer having a cellulose backbone, cationized cellulose derivatives are given, and specifically one or more selected from the group consisting of cationized cellulose, cationized hydroxyethyl cellulose, cationized hydroxypropyl cellulose, and cationized carboxymethyl cellulose, are given. Among these, cationized hydroxyethyl cellulose is preferable from the viewpoint of forming a complex gel film.

In addition, as the cationic polymer having a cellulose backbone, it preferably contains hydrophobic cationized cellulose from the viewpoint of further improving the shape fixing ability of the hair.

As the hydrophobic cationized cellulose of the component (C), hydrophobic cationized hydroxyethyl cellulose and hydrophobic cationized hydroxypropyl cellulose are given, and hydrophobic cationized hydroxyethyl cellulose is preferable.

As the hydrophobic cationized hydroxyethyl cellulose, it preferably has an anhydroglucose-derived main chain represented by the following formula (3), from the viewpoint of further improving the shape fixing ability of the hair, and the average number of moles of the cationized ethyleneoxy groups per anhydroglucose unit is 0.01 or more and 3.0 or less, and the average number of moles of ethyleneoxy groups is 0.5 or more and 4.0 or less.

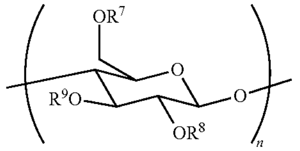

(3)

In the formula (3), $R^7$, $R^8$ and $R^9$ each independently represent a substituent having a cationized ethyleneoxy group and an ethyleneoxy group represented by the following formula (4); n is the average degree of polymerization of anhydroglucose and represents a number of 50 or more and 5000 or less.

$R^7$, $R^8$ and $R^9$ in the formula (3) are groups represented by the formula (4) and may be the same or different. In addition, n $R^7$s, n $R^8$s, and n $R^9$s may be the same or different.

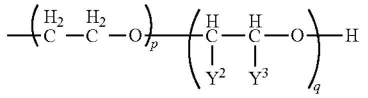

(4)

In the formula (4), one of $Y^2$ and $Y^3$ is a hydrogen atom and the other is a cationic group represented by the following formula (5). p is the number of ethyleneoxy groups contained in the formula (4), and q is the number of cationized ethyleneoxy groups ($-CH(Y^2)-CH(Y^3)-O-$) contained in the formula (4), and is respectively 0 or a positive integer. When neither p nor q is 0, the order of addition of the cationised ethyleneoxy groups to the ethyleneoxy groups is not specified, and furthermore, when p and/or q is 2 or more, they can be block or random bonded. When a plurality of substituents represented by the formula (4) are present in the molecule, the values of p and q may differ between the substituents, but at least one of them has q of 1 or more.

(5)

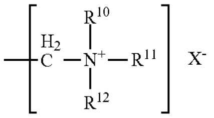

In the formula (5), $R^{10}$ to $R^{12}$ each independently represents a linear or branched alkyl group having 1 or more and 18 or less carbon atoms, and X represents an anionic group. However, at least one of $R^{12}$s present in the molecule is a linear or branched alkyl group having 8 or more and 18 or less carbon atoms.

In the formula (5), as $R^{10}$ to $R^{12}$, methyl group, ethyl group, n-propyl group, n-butyl group, n-octyl group, n-decyl group, n-dodecyl group, n-tetradecyl group, n-hexadecyl group and an n-octadecyl group are given. As $R^{10}$ and $R^{11}$, methyl group, ethyl group, n-propyl group, n-butyl group, n-octyl group, n-decyl group and n-dodecyl group are preferable, and methyl group is more preferable. As $R^{12}$, methyl group, n-octyl group, n-decyl group, and n-dodecyl group are preferable, and methyl group and n-dodecyl group are more preferable.

In the formula (5), X is an anionic group that is a counter ion of ammonium, and as the specific examples thereof, an alkyl sulfate ion, a sulfate ion, a phosphate ion, an alkyl carbonate ion, and a halide ion are given. Among these, the halide ion is preferable from the viewpoint of ease of production. As the halide ion, a fluoride ion, a chloride ion, a bromide ion and an iodide ion, are given, however, a chloride ion and a bromide ion are preferable, and a chloride ion is more preferable, from the viewpoint of the water solubility and chemical stability of the component (C).

As the component (C), commercially available polymers can also be used. As the cationic polymer having a cellulose backbone, a quaternary ammonium salt polymer (INCI name: Polyquaternium-67) obtained by addition reaction of trimethylammonium-substituted epoxide and lauryldimethylammonium-substituted epoxide to hydroxyethyl cellulose; a quaternary ammonium salt polymer (INCI name: Polyquaternium-10) obtained by adding glycidyltrimethylammonium chloride to hydroxyethyl cellulose; a quaternary ammonium salt polymer (INCI Name: Polyquaternium-24) obtained by addition polymerization of glycidyllauryldimethylammonium chloride to hydroxyethyl cellulose; a polymer of quaternary ammonium salt (INCI name: Polyquaternium-72) obtained by addition reaction of coconut oil alkyldimethylammonium-substituted epoxide to hydroxyethyl cellulose; "Caticello L-150" manufactured by Kao Corporation, and the like are given.

Among these, at least one selected from polyquaternium-67 and polyquaternium-10 are preferable, and polyquaternium-67 is more preferable.

The component (C) may be used alone or in combination of two or more.

The content of the component (C) in the hair cosmetic of the present invention is preferably 0.01% by mass or more, more preferably 0.05% by mass or more, still more preferably 0.08% by mass or more, still more preferably 0.10% by mass or more, still more preferably 0.15% by mass or more, still more preferably 0.20% by mass or more, from the viewpoint of further improving the shape fixing ability of the hair, and is preferably 5.0% by mass or less, more preferably 3.0% by mass or less, still more preferably 1.0% by mass or less, still more preferably 0.80% by mass or less, still more preferably 0.70% by mass or less, from the same viewpoint.

Taking these points together, the content of the component (C) in the hair cosmetic of the present invention is preferably 0.01% by mass or more and 5.0% by mass or less, more preferably 0.05% by mass or more and 3.0% by mass or less, still more preferably 0.08% by mass or more and 1.0% by mass or less, still more preferably 0.10% by mass or more and 0.80% by mass or less, still more preferably 0.15% by mass or more and 0.70% by mass or less, still more preferably 0.20% by mass or more and 0.70% by mass or less.

<Component (D)>

The hair cosmetic of the present invention contains a cross-linked cationic vinyl polymer as the component (D).

As the cross-linked cationic vinyl polymer of the component (D), for example, a cross-linked cationic vinyl polymer obtained by copolymerizing the following monomers (d1) to (d3).

(Monomer (d1))

The monomer (d1) is at least one selected from monomers represented by the following formula (1).

(1)

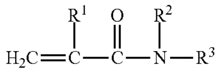

In the formula (1), $R^1$ represents a hydrogen atom or a methyl group; $R^2$ represents a hydrogen atom, a linear or branched alkyl group or an alkenyl group having 1 or more and 4 or less carbon atoms; and $R^3$ represents a linear or branched alkyl group or alkenyl group having 1 or more and 4 or less carbon atoms.

In the formula (1), $R^1$ preferably represents a hydrogen atom, $R^2$ preferably represents a linear or branched alkyl group having 1 or more and 4 or less carbon atoms, more preferably a linear alkyl group having 1 or more and 4 or less carbon atoms, still more preferably a methyl group; $R^3$ preferably represents a linear or branched alkyl group having 1 or more and 4 or less carbon atoms, more preferably represents a linear alkyl group having 1 or more and 4 or less carbon atoms, still more preferably represents a methyl group.

(Monomer (d2))

The monomer (d2) is at least one selected from monomers represented by the following formula (2).

(2)

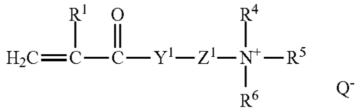

In the formula (2), $R^1$ represents a hydrogen atom or a methyl group; $R^4$ and $R^5$ each independently represents an alkyl group or alkenyl group having 1 or more and 4 or less carbon atoms; and $R^6$ is a hydrogen atom or an alkyl group having 1 or more and 4 or less carbon atoms; $Y^1$ represents —O—, —NH—, —$CH_2$— or —O—$CH_2CH(OH)$— group. When $Y^1$ is —$CH_2$—, $Z^1$ represents a single bond or a linear or branched divalent saturated hydrocarbon group having 1 or more and 3 or less carbon atoms, and when $Y^1$ is other than —$CH_2$—, $Z^1$ is a linear or branched divalent saturated hydrocarbon group having 1 or more and 4 or less carbon atoms; and Q represents a conjugate base of the acid.

In the formula (2), $R^1$ preferably represents a methyl group; $R^4$ and $R^5$ each independently, preferably represents a linear or branched alkyl group having 1 or more and 4 or less carbon atoms, more preferably represents a linear alkyl group having 1 or more and 4 or less carbon atoms, still more preferably represents a methyl group; $R^6$ preferably represents a linear alkyl group having 1 or more and 4 or less carbon atoms, more preferably an ethyl group; and $Y^1$ preferably represents —O—; $Z^1$ preferably represents a linear divalent saturated hydrocarbon group having 1 or more and 4 or less carbon atoms, more preferably an ethylene group; and Q preferably represents ethyl sulfate.

(Monomer (d3))

The monomer (d3) is a cross-linkable monomer having two or more reactive unsaturated groups. As the monomer (d3), ethylene glycol di(meth)acrylate is preferable.

As the cross-linked cationic vinyl polymer of the component (D), it preferably contains a copolymer of N,N-dimethylaminoethyl methacrylate diethyl sulfate/N,N-dimethylacrylamide/(poly)ethylene glycol dimethacrylate, more preferably a copolymer of N,N-dimethylaminoethyl methacrylate diethyl sulfate/N, N-dimethylacrylamide/(poly)ethylene glycol dimethacrylate, from the viewpoint of further improving the shape fixing ability of the hair. Here, in this specification, "(poly)ethylene glycol" means at least one selected from monoethylene glycol and polyethylene glycol. The above copolymer is called Polyquaternium-52 in International Labeling Names as the Cosmetic Ingredients (INCI name).

As the commercially available products of Polyquaternium-52, SOFCARE KG-101W-E, SOFCARE KG-301W (manufactured by Kao Corporation), and the like are given.

The component (D) may be used alone or in combination of two or more.

The content of the component (D) in the hair cosmetic of the present invention is preferably 0.01% by mass or more, more preferably 0.03% by mass or more, still more preferably 0.05% by mass or more, still more preferably 0.08% by mass or more, still more preferably 0.10% by mass or more, still more preferably 0.15% by mass or more, still more preferably 0.20% by mass or more, from the viewpoint of further improving the shape fixing ability of the hair, and is preferably 5.0% by mass or less, more preferably 3.0% by mass or less, still more preferably 1.0% by mass or less, still more preferably 0.80% by mass or less, still more preferably 0.70% by mass or less, from the same viewpoint. Taking these points together, the content of the component (D) in the hair cosmetic of the present invention is preferably 0.01% by mass or more and 5.0% by mass or less, more preferably 0.03% by mass or more and 3.0% by mass or less, still more preferably 0.05% by mass or more and 1.0% by mass or less, still more preferably 0.08% by mass or more and 0.80% by mass or less, still more preferably 0.10% by mass or more and 0.70% by mass or less, still more preferably 0.15% by mass or more and 0.70% by mass or less, still more preferably 0.20% by mass or more and 0.70% by mass or less.

In the hair cosmetic of the present invention, the mass ratio ((A)/(B)) of the component (A) with respect to the component (B) is preferably 0.01 or more, more preferably 0.03 or more, still more preferably 0.04 or more, still more preferably 0.05 or more, still more preferably 0.06 or more, from the viewpoint of further improving the shape fixing ability of the hair, and is preferably 5.0 or less, more preferably 3.0 or less, still more preferably 2.5 or less, still more preferably 2.0 or less, still more preferably 1.5 or less, still more preferably 1.2 or less, from the same viewpoint. Taking these points together, the mass ratio ((A)/(B)) of the component (A) with respect to the component (B) is preferably 0.01 or more and 5.0 or less, more preferably 0.03 or more and 3.0 or less, still more preferably 0.04 or more and 2.5 or less, still more preferably 0.05 or more and 2.0 or less, still more preferably 0.06 or more and 1.5 or less, still more preferably 0.06 or more and 1.2 or less.

In the hair cosmetic of the present invention, the mass ratio ((A)/(C)) of the component (A) with respect to the component (C) is preferably 0.10 or more, more preferably 0.20 or more, still more preferably 0.30 or more, still more preferably 0.40 or more, still more preferably 0.50 or more, from the viewpoint of further improving the shape fixing ability of the hair, and is preferably 12 or less, more preferably 8.0 or less, still more preferably 6.0 or less, still more preferably 4.0 or less, still more preferably 3.0 or less, from the same viewpoint. Taking these points together, the mass ratio ((A)/(C)) of the component (A) with respect to the component (C) is preferably 0.10 or more and 12 or less, more preferably 0.20 or more and 8.0 or less, still more preferably 0.30 or more and 6.0 or less, still more preferably 0.40 or more and 4.0 or less, still more preferably 0.50 or more and 3.0 or less.

In the hair cosmetic of the present invention, the mass ratio ((A)/(D)) of the component (A) with respect to the component (D) is preferably 0.10 or more, more preferably 0.20 or more, still more preferably 0.30 or more, still more preferably 0.40 or more, still more preferably 0.50 or more, from the viewpoint of further improving the shape fixing ability of the hair, and is preferably 12 or less, more preferably 8.0 or less, still more preferably 6.0 or less, still more preferably 4.0 or less, still more preferably 3.0 or less, from the same viewpoint. Taking these points together, the mass ratio ((A)/(D)) of the component (A) with respect to the component (D) is preferably 0.10 or more and 12 or less, more preferably 0.20 or more and 8.0 or less, still more preferably 0.30 or more and 6.0 or less, still more preferably 0.40 or more and 4.0 or less, still more preferably 0.50 or more and 3.0 or less.

In the hair cosmetic of the present invention, the mass ratio ((D)/(C)) of the component (D) with respect to the component (C) is preferably 0.10 or more, more preferably 0.20 or more, still more preferably 0.30 or more, still more preferably 0.40 or more, still more preferably 0.50 or more, still more preferably 0.80 or more, from the viewpoint of further improving the shape fixing ability of the hair, and is preferably 5.0 or less, more preferably 3.0 or less, still more preferably 2.5 or less, still more preferably 2.0 or less, still more preferably 1.5 or less, still more preferably 1.2 or less, from the same viewpoint. Taking these points together, the mass ratio ((D)/(C)) of the component (D) with respect to the component (C) is preferably 0.10 or more and 5.0 or less, more preferably 0.20 or more and 3.0 or less, still more preferably 0.30 or more and 2.5 or less, still more preferably 0.40 or more and 2.0 or less, still more preferably 0.50 or more and 1.5 or less, still more preferably 0.80 or more and 1.2 or less.

The total content of the components (A) to (D) in the hair cosmetic of the present invention is preferably 0.5% by mass or more, more preferably 1.0% by mass or more, still more preferably 1.2% by mass or more, still more preferably 1.5% by mass or more, and is preferably 25% by mass or less, more preferably 20% by mass or less, still more preferably 15% by mass or less, still more preferably 12% by mass or less, still more preferably 10% by mass or less, from the viewpoint of further improving the shape fixing ability of the hair. Taking these points together, the total content of the components (A) to (D) in the hair cosmetic of the present invention is preferably 0.5% by mass or more and 25% by mass or less, more preferably 1.0% by mass or more and 20% by mass or less, more preferably 1.2% by mass or more and 15% by mass or less, still more preferably 1.5% by mass or more and 12% by mass or less, still more preferably 1.5% by mass or more and 10% by mass or less.

Other Components

The hair cosmetic of the present invention may contain an aqueous medium from the viewpoint of handling and facilitating to exhibit the effects of action of the components (A) to (D), depending on its form, formulation and the like. As the aqueous medium, for example, water, low alcohols such ethanol, and isopropyl alcohol; low molecular diols and triols and the like having 6 or less of carbon atoms such as 1,3-butylene glycol, glycerin, ethylene glycol, propylene glycol, and dipropylene glycol; and the like are given. One of these may be used alone or in combination with two or more of them. Among these, it preferably contains water as the aqueous medium.

The content of the aqueous medium in the hair cosmetic of the present invention is preferably 60% by mass or more, more preferably 65% by mass or more, still more preferably 70% by mass or more, still more preferably 75% by mass or more, from the viewpoint of adjusting the hair cosmetic to an appropriate concentration and viscosity, and is preferably 99% by mass or less, more preferably 98% by mass or less, still more preferably 97% by mass or less, still more preferably 96% by mass or less, from the same viewpoint. Taking these viewpoints together, the content of the aqueous medium in the hair cosmetic of the present invention is preferably 60% by mass or more and 99% by mass or less, more preferably 65% by mass or more and 98% by mass or less, still more preferably 70% by mass or more and 97% by mass or less, still more preferably 75% by mass or more and 96% by mass or less.

Further, the hair cosmetic of the present invention may also contain other components within a range where the purpose of the present invention is not impaired. As the components, for example, nonionic surfactants, amphoteric surfactants, and other components which are usually blended in hair cosmetics, such as pH adjusters, aromatic alcohols, antioxidants, oil agents, polymers other than the components (A) to (D), anti-dandruff agents, vitamins, bactericides, anti-inflammatory agents, preservatives, chelating agents, moisturizing agents, ceramides, coloring agents, *eucalyptus* polar solvent extracts, proteins or hydrolysates obtained from shells having a pearl layer or pearls, honey, royal jelly, proteins or hydrolysates obtained from silk, protein-containing extracts obtained from legume seeds, *panax ginseng* extracts, rice germ extracts, fucus extracts, aloe extract, lotus extract, pomegranate extract, rose extract, *chamomilla* extract, licorice extract, gettou (shell ginger) leaf extract, *chlorella* extract, pearling agent, fragrance, pigment, UV absorber, shea butter, rose water, orange oil, *eucalyptus* oil, and organic acids, are given.

The pH of the hair cosmetic of the present invention is not particularly limited as long as it is within the range generally applicable for use as a hair cosmetic, but the pH of the hair cosmetic is controlled to be preferably 3.0 or more, more preferably 4.0 or more, still more preferably 5.0 or more; and preferably 12.0 or less, more preferably 11.0 or less, still more preferably 10.0 or less, by the addition of an acid or a base, from the viewpoint of controlling the damage to the hair and the scalp and facilitating to exhibit the effects of the present invention. Taking these viewpoints together, the pH of the hair cosmetic of the present invention is preferably 3.0 or more and 12.0 or less, more preferably 4.0 or more and 11.0 or less, still more preferably 5.0 or more and 10.0 or less. Note that the pH of the hair cosmetic is the measurement value at 25 °C.

<Manufacturing Method>

The hair cosmetic of the present invention can be produced by a conventional method. For example, it can be produced by blending the components (A) to (D) and, if necessary, other components, and mixing them using a known stirring device or the like.

[Hair Treatment Method]

The hair treatment method of the present invention contains a step of applying the above hair cosmetic of the present invention to the hair, and a step of rinsing the hair in which the hair cosmetic is applied, with water.

As the method for applying the hair cosmetic to the hair, for example, applying, spraying or casting to the hair, immersing the hair into the hair cosmetic, and the like, are given. The hair to be applied may be dry or wet, preferably in the wet state by being washed after being combed with a brush, comb and the like. The application of the hair cosmetic may be applying or rubbing by hand, or performing by using a brush, comb, and the like. Moreover, the hair to which the hair cosmetic is applied may be the entire hair or part of the hair.

The amount of the hair cosmetic applied to the hair is preferably 0.01 or more, more preferably 0.03 or more, still more preferably 0.05 or more, still more preferably 0.08 or more; preferably 20 or less, more preferably 15 or less, still more preferably 10 or less, still more preferably 5 or less, still more preferably 1 or less, still more preferably 0.5 or less, as a bath ratio with respect to the mass of the hair to be applied (mass of the hair cosmetic/mass of the hair to be applied). Taking these viewpoints together, as the amount of the hair cosmetic applied to the hair is preferably 0.01 or more and 20 or less, more preferably 0.03 or more and 15 or less, still more preferably 0.05 or more and 10 or less, still more preferably 0.08 or more and 5 or less, still more preferably 0.08 or more and 1 or less, still more preferably 0.08 or more and 0.5 or less, as a bath ratio with respect to the mass of the hair to be applied (mass of the hair cosmetic/mass of the hair to be applied).

After the above step, it is preferable to perform a step of rinsing the hair to which the hair cosmetic was applied, with water. In this case, it is preferable to rinse the hair with water after absorbing the hair cosmetic into the entire hair so that the hair cosmetic can be sufficiently absorbed into the hair. The applying time is preferably 15 seconds or longer, more preferably 30 seconds or longer; and is preferably 5 minutes or shorter, more preferably 3 minutes or shorter. Taking these viewpoints together, the applying time is preferably 15 seconds or longer and 5 minutes or shorter, more preferably 30 seconds or longer and 3 minutes or shorter.

The step of rinsing with water is sufficient as long as it can remove the excess hair cosmetics from the surface of the hair, and the rinsing time is preferably 5 seconds or longer and 3 minutes or shorter. The temperature of the water may be such that it does not burden the body, is preferably 15 °C or higher and 50 °C or lower, more preferably 25 °C or higher and 45 °C or lower.

The hair after the washing with water, is dried by a natural drying by towel drying and the like, or by a forced drying by using a dryer and the like. By treating the hair, especially the peculiar hair, using the hair cosmetic of the present invention as described above, it is possible to impart a certain shape by bundling the hair, and improve the shape fixing ability of the hair for fixing the shape of the bundled hair. Therefore, for the peculiar hair particularly, it can be reduced the time and the effort required in hairstyling, and is suitable to be applied.

In relation to the aforementioned embodiments, the preferable embodiments of the hair cosmetic of the present invention will be further disclosed as follows.

<1> A hair cosmetic containing the following components (A) to (D):

(A) an anionic polymer;

(B) an anionic surfactant;

(C) a cationic polymer having a cellulose backbone; and (D) a cross-linked cationic vinyl polymer.

<2> The hair cosmetic according to the item <1>, in which, the component (D) contains a cross-linked cationic vinyl polymer obtained by copolymerizing the following monomers (d1) to (d3):

(d1) at least one selected from monomers represented by the following formula (1);

(1)

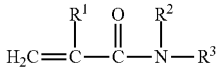

(in the formula (1), $R^1$ represents a hydrogen atom or a methyl group; $R^2$ represents a hydrogen atom, a linear or branched alkyl group or alkenyl group having 1 or more and 4 or less carbon atoms; and $R^3$ represents a linear or branched alkyl group or alkenyl group having 1 or more and 4 or less carbon atoms, and in which, $R^1$ preferably represents a hydrogen atom; $R^2$ preferably represents a linear or branched alkyl group having 1 or more and 4 or less carbon atoms, more preferably represents a linear alkyl group having 1 or more and 4 or less carbon atoms, still more preferably represents a methyl group; $R^3$ preferably represents a linear or branched alkyl group having 1 or more and 4 or less carbon atoms, more preferably represents a linear alkyl group having 1 or more and 4 or less carbon atoms, still more preferably represents a methyl group) and, (d2) at least one selected from monomers represented by the following formula (2);

(2)

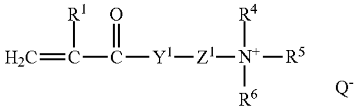

(in the formula (2), $R^1$ represents a hydrogen atom or a methyl group; $R^4$ and $R^5$ each independently represent an alkyl group or an alkenyl group having 1 or more and 4 or less carbon atoms; and $R^6$ is a hydrogen atom or an alkyl group having 1 or more and 4 or less carbon atoms; $Y^1$ is —O—, —NH—, —$CH_2$— or —O—$CH_2CH(OH)$— group, and when $Y^1$ is —$CH_2$—, $Z^1$ represents a single bond or a linear or branched divalent saturated hydrocarbon group having 1 or more and 3 or less carbon atoms, and when $Y^1$ is other than —$CH_2$—, $Z^1$ represents a linear or branched divalent saturated hydrocarbon group having 1 or more and 4 or less carbon atoms; and Q represents a conjugate base of the acid, and in the formula (2), $R^1$ preferably represents a methyl group; $R^4$ and $R^5$ each independently preferably represent a linear or branched alkyl group having 1 or more and 4 or less carbon atoms, more preferably represent a linear alkyl group having 1 or more and 4 or less carbon atoms, still more preferably represent a methyl group; and $R^6$ preferably represents a linear alkyl group having 1 or more and 4 or less carbon atoms, more preferably represents an ethyl group; $Y^1$ preferably represents —O—, $Z^1$ preferably represents a linear divalent saturated hydrocarbon group having 1 or more and 4 or less carbon atoms, more preferably represents an ethylene group; and Q preferably represents ethyl sulfate) and, (d3) a cross-linkable monomer having two or more reactive unsaturated groups, preferably ethylene glycol di(meth)acrylate.

<3> The hair cosmetic according to the item <1> or <2>, in which, the component (D) preferably contains a copolymer of N,N-dimethylaminoethyl methacrylate diethyl sulfate/N, N-dimethylacrylamide/(poly)ethylene glycol dimethacrylate, is more preferably a copolymer of N,N-dimethylaminoethyl methacrylate diethyl sulfate/N, N-dimethylacrylamide/(poly)ethylene glycol dimethacrylate.

<4> The hair cosmetic according to any one of the items <1> to <3>, in which the component (A) preferably contains a vinyl-based polymer having a carboxy group or a sulfonic acid group as an anionic group, more preferably contains a vinyl-based polymer having a carboxy group, still more preferably contains a vinyl-based polymer containing structural units derived from crotonic acid, maleic acid, maleic acid monoester, itaconic acid, or (meth)acrylic acid, still more preferably contains at least one selected from cross-linked polyacrylic acid and (acrylates/alkyl acrylate (C10-30)) crosspolymer, still more preferably contains cross-linked polyacrylic acid, still more preferably contains a carboxyvinyl polymer, that is, a polymer of acrylic acid cross-linked with pentaerythyl allyl ether, sucrose allyl ether or propylene allyl ether.

<5> The hair cosmetic according to any one of the items <1> to <4>, in which, the component (B) preferably contains at least one selected from polyoxyethylene alkyl ether sulfate, alkyl benzene sulfonate, α-olefin sulfonate, internal olefin sulfonate, alkyl or alkenyl sulfate, alkyl sulfonate, saturated or unsaturated fatty acid salt, alkyl or alkenyl ether carboxylic acid salts, α-sulfo fatty acid salts, N-acylamino acid salts, phosphoric acid mono- or diester salts, and sulfosuccinic acid ester salts; more preferably contains at least one selected from the group consisting of α-olefin sulfonates, internal olefin sulfonates and polyoxyethylene alkyl ether sulfates; still more preferably contains at least one selected from the group consisting of α-olefin sulfonates and polyoxyethylene alkyl ether sulfates; still more preferably contains polyoxyethylene alkyl ether sulfate, still more preferably contains polyoxyethylene alkyl ether sulfate represented by the following formula (I); still more preferably contains at least one selected from sodium laureth sulfate and ammonium laureth sulfate, $$R^1—O—(CH_2CH_2O)_p—SO_3Y \quad (I)$$

in the formula (I), $R^1$ represents a linear or branched alkyl group having 8 or more and 22 or less carbon atoms; p represents the average number of added moles and is a number of 0.25 or more and 20 or less; Y represents an alkali metal, an alkaline earth metal, ammonium, alkanolamine or basic amino acid.

<6> The hair cosmetic according to any one of the items <1> to <5>, in which the component (C) preferably contains a cationized cellulose derivative, more preferably contains at least one selected from cationized cellulose, cationized hydroxyethyl cellulose, cationized hydroxypropyl cellulose, and cationized carboxymethyl cellulose, and still more preferably contains cationized hydroxyethyl cellulose.

<7> The hair cosmetic according to any one of the items <1> to <6>, in which the component (C) preferably contains hydrophobic cationized cellulose; more preferably contains at least one selected from hydrophobic cationized hydroxyethyl cellulose and hydrophobic cationized hydroxypropyl cellulose; still more preferably contains hydrophobic cationized hydroxyethyl cellulose; still more preferably has an anhydroglucose-derived main chain represented by the formula (3), has the average number of moles of cationized ethyleneoxy groups per anhydroglucose unit being 0.01 or more and 3.0 or less, and contains a hydrophobic cationized hydroxyethyl cellulose, in which an average number of moles of the ethyleneoxy groups of 0.5 or more and 4.0 or less.

<8> The hair cosmetic according to any one of items <1> to <7>, in which the component (C) preferably contains at least one selected from a polymer of quaternary ammonium salts (INCI name: polyquaternium-67) obtained by the addition reaction of trimethylammonium-substituted epoxide and lauryl dimethylammonium-substituted epoxide to hydroxyethylcellulose, a polymer of quaternary ammonium salts (INCI name: Polyquaternium-10) obtained by adding glycidyltrimethylammonium chloride to hydroxyethyl cellulose, a polymer of quaternary ammonium salts (INCI name: Polyquaternium-24) obtained by addition polymerization of glycidyl lauryl dimethyl ammonium chloride to hydroxyethyl cellulose, and a polymer of quaternary ammonium salts (INCI name: Polyquaternium-72) obtained by the addition reaction of coconut oil alkyldimethylammonium substituted epoxide to hydroxyethyl cellulose; more preferably contains at least one selected from polyquaternium-67 and polyquaternium-10; still more preferably contains polyquaternium-67.

<9> The hair cosmetic according to any one of the items <1> to <8>, in which the mass ratio ((A)/(D)) of the component (A) with respect to the component (D) is preferably 0.10 or more, more preferably 0.20 or more, still more preferably 0.30 or more, still more preferably is 0.40 or more, still more preferably 0.50 or more; and is preferably 12 or less, more preferably 8.0 or less, still more preferably 6.0 or less, still more preferably 4.0 or less, still more preferably 3.0 or less.

<10> The hair cosmetic according to any one of the items <1> to <9>, in which the mass ratio ((A)/(B)) of the component (A) with respect to the component (B) is preferably 0.01 or more, more preferably 0.03 or more, still more preferably 0.04 or more, still more preferably 0.05 or more, still more preferably 0.06 or more; and preferably 5.0 or less, more preferably 3.0 or less, still more preferably 2.5 or less, still more preferably 2.0 or less, still more preferably 1.5 or less, still more preferably 1.2 or less.

<11> The hair cosmetic according to any one of the items <1> to <10>, in which the mass ratio ((A)/(C)) of the component (A) with respect to the component (C) is preferably 0.10 or more, more preferably 0.20 or more, still more preferably 0.30 or more, still more preferably 0.40 or more, still more preferably 0.50 or more; and preferably 12 or less, more preferably 8.0 or less, still more preferably 6.0 or less, still more preferably 4.0 or less, still more preferably 3.0 or less.

<12> The hair cosmetic according to any one of the items <1> to <11>, in which the mass ratio ((D)/(C)) of the component (D) with respect to the component (C) is preferably 0.10 or more, more preferably 0.20 or more, still more preferably 0.30 or more, still more preferably 0.40 or more, still more preferably 0.50 or more, still more preferably 0.80 or more; and preferably 5.0 or less, more preferably 3.0 or less, still more preferably 2.5 or less, still more preferably 2.0 or less, still more preferably 1.5 or less, still more preferably 1.2 or less.

<13> The hair cosmetic according to any one of the items <1> to <12>, in which the total content of the components (A) to (D) is preferably 0.5% by mass or more, more preferably 1.0% by mass or more, still more preferably 1.2% by mass or more, still more preferably 1.5% by mass or more; and preferably 25% by mass or less, more preferably 20% by mass or less, still more preferably 15% by mass or less, still more preferably 12% by mass or less, still more preferably 10% by mass or less.

<14> The hair cosmetic according to any one of the items <1> to <13>, in which the content of the component (A) is preferably 0.01% by mass or more, more preferably 0.03% by mass or more, still more preferably 0.05% by mass or more, still more preferably 0.08% by mass or more, still more preferably 0.10% by mass or more, still more preferably 0.20% by mass or mor; and preferably 5.0% by mass or less, more preferably 3.0% by mass or less, still more preferably 1.0% by mass or less, and still more preferably 0.80% by mass or less.

<15> The hair cosmetic according to any one of the items <1> to <14>, in which the content of the component (B) is preferably 0.1% by mass or more, more preferably 0.2% by mass or more, still more preferably 0.3% by mass or more, still more preferably 0.4% by mass or more, still more preferably 0.5% by mass or more; and preferably 20% by mass or less, more preferably 15% by mass or less, still more preferably 13% by mass or less, still more preferably 10% by mass or less, still more preferably 8.0% by mass or less, still more preferably 6.0% by mass or less.

<16> The hair cosmetic according to any one of the items <1> to <15>, in which the content of the component (C) is preferably 0.01% by mass or more, more preferably 0.05% by mass or more, still more preferably 0.08% by mass or more, still more preferably 0.10% by mass or more, still more preferably 0.15% by mass or more, still more preferably 0.20% by mass or more; and preferably 5.0% by mass or less, more preferably 3.0% by mass or less, still more preferably 1.0% by mass or less, still more preferably 0.80% by mass or less, still more preferably 0.70% by mass or less.

<17> The hair cosmetic according to any one of the items <1> to <16>, in which the content of the component (D) is preferably 0.01% by mass or more, more preferably 0.03% by mass or more, and still more preferably 0.05% by mass or more, still more preferably 0.08% by mass or more, still more preferably 0.10% by mass or more, still more preferably 0.15% by mass or more, still more preferably 0.20% by mass or more; and preferably 5.0% by mass or less, more preferably 3.0% by mass or less, still more preferably 1.0% by mass or less, still more preferably 0.80% by mass or less, still more preferably 0.70% by mass or less. <18> The hair cosmetic according to any one of the items <1> to <17>, in which the pH of the hair cosmetic is preferably 3.0 or more, more preferably 4.0 or more, still more preferably 5.0 or more; and preferably 12.0 or less, more preferably 11.0 or less, still more preferably 10.0 or less.

<19> The hair cosmetic according to any one of the items <1> to <18>, containing an aqueous medium.

<20> The hair cosmetic according to the item <19>, in which the aqueous medium preferably contains at least one selected from water, ethanol, isopropyl alcohol, 1,3-butylene glycol, glycerin, ethylene glycol, propylene glycol, and dipropylene glycol, more preferably contains water.

<21> The hair cosmetic according to item <19> or <20>, in which the content of the aqueous medium is preferably 60% by mass or more, more preferably 65% by mass or more, still more preferably 70% by mass or more, still more preferably 75% by mass or more; and preferably 99% by mass or less, more preferably 98% by mass or less, still more preferably 97% by mass or less, still more preferably 96% by mass or less.

<22> The hair cosmetic according to any one of the items <1> to <21>, which is preferably a hair shampoo, a hair rinse, a hair conditioner, a hair treatment, a hair pack, or a hair styling agent, more preferably a hair rinse, a hair conditioner, a hair treatment, a hair pack, or a hair styling agent.

<23> The hair cosmetic according to any one of the items <1> to <22>, which is preferably liquid, foam, paste or cream, more preferably liquid, paste or cream, still more preferably liquid.

<24> A hair treatment method containing: a step of applying the hair cosmetic according to any one of the items <1> to <23> to a hair; and a step of rinsing the hair in which the hair cosmetic is applied, with water.

<25> Use of the hair cosmetic according to any one of the items <1> to <23>, which is for fixing the shape of the hair.

<26> A method of fixing the shape of the hair, in which the hair cosmetic according to any one of the items <1> to <23> is applied.

EXAMPLES

Examples 1 to 28, Comparative Examples 1 to 5

The hair cosmetic having the compositions of each Example and each Comparative Example shown in Tables 1 to 4 below was prepared, and the hair bundle for the evaluation was used to evaluate the shape fixing ability of the hair. The evaluation results are shown in Tables 1 to 4.

<Method of Blending Hair Cosmetics>

Examples 1 to 23, Comparative Examples 1 to 5

The one in which the component (C) or guar hydroxypropyltrimonium chloride and the component (D) were dissolved or uniformly dispersed in water, moderate amount of water, and the component (B) were placed in a beaker, and these components were uniformly mixed at 80 °C. The component (A) uniformly dispersed in water is added to the obtained mixture, cooled to room temperature and uniformly mixed, and the pH is adjusted to 6 (measurement temperature: 25 °C.) using a pH adjuster (sodium hydroxide) to obtain each hair cosmetic. Here, the mixing ratio of each component is as shown in Tables 1 to 3.

Examples 24 to 28

The one in which the component (C) and the component (D) were dissolved or uniformly dispersed in water, moderate amount of water, the component (B), and lauramidopropyl betaine were placed in a beaker, and these components were uniformly mixed at 80 °C. A mixture in which lanolin fatty acid, stearoxypropyldimethylamine, benzyl alcohol, and 2-phenoxyethanol were dissolved by heating at 60 °C, was added to the obtained mixture, and the component (A) uniformly dispersed in water was further added. In addition, it was cooled to room temperature and mixed uniformly. Furthermore, (bisisobutyl PEG-14/amodimethicone) copolymer and/or quaternium-80 were added and mixed uniformly, malic acid was added, and finally the pH was adjusted to 6 or 9.5 (measuring temperature: 25 °C) using a pH adjuster (sodium hydroxide) to obtain each hair cosmetic. Here, the mixing ratio of each component is as shown in Table 4.

<Evaluation of the Shape Fixing Ability of the Hair>

A curly hair bundle having a mass of 2 g and a length of 35 cm was washed with a plain shampoo having the composition shown below and thoroughly rinsed with warm water (35-40 °C). Next, 0.2 g of the hair cosmetic having the composition shown in each example and each comparative example was applied to this hair bundle and allowed to stand for 1 minute. Then, the hair bundle to which the hair cosmetic was applied was rinsed with warm water (35-40 °C) for 30 seconds. Thereafter, the bundle was styled into straight with a ring comb, dried with a towel, and completely dried with a dryer equipped with a diffuser to obtain the hair bundle for the evaluation.

The length of the obtained hair bundle for the evaluation and the bundle width at a point of 20 cm from the base of the hair bundle were measured to evaluate the shape fixing ability of the hair. The fixing ability in the width direction of the hair bundle was evaluated by the bundle width (cm). The fixing ability in the lengthwise direction of the hair bundle was evaluated by Δ length (cm)=(length of the bundle when stretched before treatment)−(length of the bundle after treatment). It means that the smaller the bundle width and the Δ length, the better the shape fixing ability of the hair bundle.

Here, "the length of the hair bundle when stretched before treatment" is the length when the curly hair bundle before treatment is lightly stretched by hand and the curled hair bundle is straightened.

(Composition of Plain Shampoo)

| | [Unit: % by mass] |
|---|---|
| Sodium polyoxyethylene(2.5) lauryl ether sulfate | 15.5 |
| Lauric acid diethanolamide | 2.3 |
| Disodium edetate | 0.15 |
| Sodium benzoate | 0.5 |
| Sodium chloride | 0.8 |
| Phosphoric acid | Moderate (pH adjustment) |

-continued

| | [Unit: % by mass] |
|---|---|
| Fragrance | Trace amount (Less than 0.5) |
| Methylparaben | Trace amount (Less than 0.5) |
| Water | Balance |
| (pH 7.0) | Total 100.0 |

TABLE 1

| | | | Example | | | | | | | | |
|---|---|---|---|---|---|---|---|---|---|---|---|
| | | | 1 | 2 | 3 | 4 | 5 | 6 | 7 | 8 | 9 |
| Blending (% by mass) | (A) | Carbomer (*1) | 0.05 | 0.10 | 0.30 | 0.50 | — | 0.50 | 0.70 | 0.50 | 0.50 |
| | | (Acrylates/alkyl acrylate (C10-30)) crosspolymer (*2) | — | — | — | — | 0.50 | — | — | — | — |
| | (B) | Ammonium laureth sulfate (*3) | 2.00 | 2.00 | 2.00 | 2.00 | 2.00 | 0.50 | 2.00 | 2.00 | 4.00 |
| | (C) | Polyquaternium-67 (*4) | 0.30 | 0.30 | 0.30 | 0.30 | 0.30 | 0.30 | 0.30 | — | 0.30 |
| | | Polyquaternium-10 (*5) | — | — | — | — | — | — | — | 0.30 | — |
| | (D) | Polyquaternium-52 (*6) | 0.30 | 0.30 | 0.30 | 0.30 | 0.30 | 0.30 | 0.30 | 0.30 | 0.30 |
| | Others | Guar hydroxypropyltrimonium chloride (*7) | — | — | — | — | — | — | — | — | — |
| | | pH adjuster | Moderate | | | | | | | | |
| | | Purified water | Balance | | | | | | | | |
| | | Tatal | 100 | 100 | 100 | 100 | 100 | 100 | 100 | 100 | 100 |
| | | pH | 6 | | | | | | | | |
| | | Mass ratio (A)/(B) | 0.03 | 0.05 | 0.15 | 0.25 | 0.25 | 1.00 | 0.35 | 0.25 | 0.13 |
| | | Mass ratio (A)/(C) | 0.17 | 0.33 | 1.00 | 1.67 | 1.67 | 1.67 | 2.33 | 1.67 | 1.67 |
| | | Mass ratio (A)/(D) | 0.17 | 0.33 | 1.00 | 1.67 | 1.67 | 1.67 | 2.33 | 1.67 | 1.67 |
| | | Mass ratio (D)/(C) | 1.00 | 1.00 | 1.00 | 1.00 | 1.00 | 1.00 | 1.00 | 1.00 | 1.00 |
| Evaluation | | Shape fixing ability of hair Bundle width (cm) | 0.90 | 0.80 | 0.65 | 0.60 | 0.70 | 0.60 | 0.65 | 0.70 | 0.60 |
| | | Shape fixing ability of hair Δ length (cm) | 0.0 | 0.0 | 0.5 | 0.5 | 0.0 | −0.5 | 0.0 | −0.5 | 0.0 |

| | | | Example | | | Comparative Example | | |
|---|---|---|---|---|---|---|---|---|
| | | | 10 | 11 | 12 | 1 | 2 | 3 |
| Blending (% by mass) | (A) | Carbomer (*1) | 0.50 | 0.50 | 0.50 | — | 0.50 | 0.50 |
| | | (Acrylates/alkyl acrylate (C10-30)) crosspolymer (*2) | — | — | — | — | — | — |
| | (B) | Ammonium laureth sulfate (*3) | 6.00 | 9.00 | 12.00 | 2.00 | — | 2.00 |
| | (C) | Polyquaternium-67 (*4) | 0.30 | 0.30 | 0.30 | 0.30 | 0.30 | — |
| | | Polyquaternium-10 (*5) | — | — | — | — | — | — |
| | (D) | Polyquaternium-52 (*6) | 0.30 | 0.30 | 0.30 | 0.30 | 0.30 | 0.30 |
| | Others | Guar hydroxypropyltrimonium chloride (*7) | — | — | — | — | — | 0.30 |
| | | pH adjuster | Moderate | | | | | |
| | | Purified water | Balance | | | | | |
| | | Tatal | 100 | 100 | 100 | 100 | 100 | 100 |
| | | pH | 6 | | | | | |
| | | Mass ratio (A)/(B) | 0.08 | 0.06 | 0.04 | — | — | 0.25 |
| | | Mass ratio (A)/(C) | 1.67 | 1.67 | 1.67 | — | 1.67 | — |
| | | Mass ratio (A)/(D) | 1.67 | 1.67 | 1.67 | — | 1.67 | 1.67 |
| | | Mass ratio (D)/(C) | 1.00 | 1.00 | 1.00 | 1.00 | 1.00 | — |
| Evaluation | | Shape fixing ability of hair Bundle width (cm) | 0.65 | 0.70 | 0.80 | 1.80 | 1.30 | 2.80 |
| | | Shape fixing ability of hair Δ length (cm) | −0.5 | 0.5 | 0.5 | 1.5 | 2.5 | 0.5 |

The annotations of *1 to *7 in Table 1 are shown below. In addition, % by mass in Table 1 is the amount of active ingredients.

*1 Carbopol 980 manufactured by Lubrizol Corporation

*2 Carbopol ETD2020 manufactured by Lubrizol Corporation

*3 EMAL 170S-A (70% by mass of active ingredient) manufactured by Kao Corporation

*4 SoftCAT SL-100 manufactured by Dow Chemical Company

*5 POIZ C-150L manufactured by Kao Corporation

*6 SOFCARE KG-101W-E (2.4% by mass of active ingredient) manufactured by Kao Corporation

*7 Jaguar C-14S manufactured by Solvay

TABLE 2

| | | | Example 13 | Example 14 | Example 4 | Example 15 | Example 16 | Example 17 | Example 18 | Comparative Example 4 | Comparative Example 5 |
|---|---|---|---|---|---|---|---|---|---|---|---|
| Blending (% by mass) | (A) | Carbomer (*1) | 0.50 | 0.50 | 0.50 | 0.50 | 0.50 | 0.50 | 0.50 | 0.50 | 0.50 |
| | (B) | Ammonium laureth sulfate (*2) | 2.00 | 2.00 | 2.00 | 2.00 | 2.00 | 2.00 | 2.00 | 2.00 | 2.00 |
| | (C) | Polyquaternium-67 (*3) | 0.30 | 0.30 | 0.30 | 0.10 | 0.30 | 0.50 | 0.10 | — | 0.30 |
| | (D) | Polyquaternium-52 (*4) | 0.05 | 0.10 | 0.30 | 0.50 | 0.20 | 0.50 | 0.30 | 0.30 | — |
| | Others | pH adjuster | Moderate | | | | | | | | |
| | | Purified water | Balance | | | | | | | | |
| | | Total | 100 | 100 | 100 | 100 | 100 | 100 | 100 | 100 | 100 |
| | | pH | 6 | | | | | | | | |
| | | Mass ratio (A)/(B) | 0.25 | 0.25 | 0.25 | 0.25 | 0.25 | 0.25 | 0.25 | 0.25 | 0.25 |
| | | Mass ratio (A)/(C) | 1.67 | 1.67 | 1.67 | 5.00 | 1.67 | 1.00 | 5.00 | — | — |
| | | Mass ratio (A)/(D) | 10.00 | 5.00 | 1.67 | 1.00 | 2.50 | 1.00 | 1.67 | 1.67 | 1.67 |
| | | Mass ratio (D)/(C) | 0.17 | 0.33 | 1.00 | 5.00 | 0.67 | 1.00 | 3.00 | — | — |
| Evaluation | | Shape fixing ability of hair Bundle width (cm) | 1.00 | 0.80 | 0.60 | 1.20 | 0.80 | 0.80 | 1.20 | 4.30 | 4.60 |
| | | Shape fixing ability of hair Δ Length (cm) | 0.0 | 0.0 | 0.5 | 0.5 | 0.0 | 0.0 | 0.0 | 2.5 | 1.0 |

The annotations of *1 to *4 in Table 2 are shown below. In addition, % by mass in Table 2 is the amount of active ingredients.
*1 Carbopol 980 manufactured by Lubrizol Corporation
*2 Emar 170S-A (70% by mass of active ingredient) manufactured by Kao Corporation
*3 SoftCAT SL-100 manufactured by Dow Chemical Company
*4 SOFCARE KG-101W-E (2.4% by mass of active ingredient content) manufactured by Kao Corporation.

TABLE 3

| | | | Example 4 | Example 19 | Example 20 | Example 21 | Example 22 | Example 23 |
|---|---|---|---|---|---|---|---|---|
| Blending (% by mass) | (A) | Carbomer (*1) | 0.50 | 0.50 | 0.50 | 0.50 | 0.50 | 0.50 |
| | (B) | Ammonium laureth sulfate (*2) | 2.00 | — | — | — | — | — |
| | | Sodium α-olefin sulfonate (*3) | — | 2.00 | — | — | — | — |
| | | Sodium C-16 internal olefin sulfonate DBP4.2 (*4) | — | — | 2.00 | — | — | — |
| | | Sodium C-16 internal olefin sulfonate DBP3.6 (*5) | — | — | — | 2.00 | — | — |
| | | Sodium laureth acetate (*6) | — | — | — | — | 2.00 | — |
| | | Cocoyl alanine sodium (*7) | — | — | — | — | — | 2.00 |
| | (C) | Polyquaternium-67 (*8) | 0.30 | 0.30 | 0.30 | 0.30 | 0.30 | 0.30 |
| | (D) | Polyquaternium-52 (*9) | 0.30 | 0.30 | 0.30 | 0.30 | 0.30 | 0.30 |
| | Others | pH adjuster | Moderate | | | | | |
| | | Purified water | Balance | | | | | |
| | | Total | 100 | 100 | 100 | 100 | 100 | 100 |
| | | pH | 6 | | | | | |
| | | Mass ratio (A)/(B) | 0.25 | 0.25 | 0.25 | 0.25 | 0.25 | 0.25 |
| | | Mass ratio (A)/(C) | 1.67 | 1.67 | 1.67 | 1.67 | 1.67 | 1.67 |
| | | Mass ratio (A)/(D) | 1.67 | 1.67 | 1.67 | 1.67 | 1.67 | 1.67 |
| | | Mass ratio (D)/(C) | 1.00 | 1.00 | 1.00 | 1.00 | 1.00 | 1.00 |
| Evaluation | | Shape fixing ability of hair Bundle width (cm) | 0.60 | 0.50 | 0.90 | 0.90 | 0.70 | 0.70 |
| | | Shape fixing ability of hair Δ Length (cm) | 0.5 | 0.5 | 0.5 | 1.0 | 0.0 | 1.0 |

The annotations of *1 to *9 in Table 3 are shown below. In addition, % by mass in Table 3 is the amount of active ingredients.
*1 Carbopol 980 manufactured by Lubrizol Corporation
*2 EMAL 170S-A (70% by mass of active ingredient) manufactured by Kao Corporation
*3 Bio-Terge AS-40 (40% by mass of active ingredient) manufactured by STEPAN COMPANY
*4 Manufacturing example 1
*5 Manufacturing example 2
*6 AKYPO LM-26SD (19% by mass of active ingredient) manufactured by Kao Corporation
*7 AMILITE ACS-12 (30% by mass of active ingredient) manufactured by Ajinomoto Healthy Supply Co., Inc.
*8 SoftCAT SL-100 manufactured by Dow Chemical Company
*9 SOFCARE KG-101W-E (2.4% by mass of active ingredient) manufactured by Kao Corporation

TABLE 4

| | | | Example | | | | |
|---|---|---|---|---|---|---|---|
| | | | 24 | 25 | 26 | 27 | 28 |
| Blending (% by mass) | (A) | Carbomer (*1) | 0.50 | 0.50 | 0.50 | 0.50 | 0.50 |
| | (B) | Ammonium laureth sulfate (*2) | 2.00 | — | — | — | — |
| | | Sodium laureth sulfate (*3) | — | 2.03 | — | — | — |
| | | Sodium laureth sulfate (*4) | — | — | 2.30 | — | — |
| | | Sodium C-16 internal olefin sulfonate DBP4.2 (*5) | — | — | — | 1.99 | — |
| | | Sodium α-olefin sulfonate (*6) | — | — | — | — | 1.82 |
| | (C) | Polyquaternium-67 (*7) | 0.50 | 0.50 | 0.50 | 0.50 | 0.50 |
| | (D) | Polyquaternium-52 (*8) | 0.50 | 0.50 | 0.50 | 0.50 | 0.50 |
| | Others | Lauramidopropyl Betaine (*9) | 0.33 | 0.33 | 0.33 | 0.33 | 0.33 |
| | | Lanolin fatty acid (*10) | 0.05 | 0.05 | 0.05 | 0.05 | 0.05 |
| | | Stealoxypropyldimethylamine (*11) | 0.075 | 0.075 | 0.075 | 0.075 | 0.075 |
| | | Benzyl alcohol (*12) | 0.50 | 0.50 | 0.50 | 0.50 | 0.50 |
| | | 2-Phenoxyethanol (*13) | 0.50 | 0.50 | 0.50 | 0.50 | 0.50 |
| | | (Bisisobutyl PEG-14/amodimethicone) copolymer (*14) | 0.10 | 0.10 | 0.10 | 0.10 | 0.10 |
| | | Quaternium-80 (*15) | — | 0.20 | 0.20 | 0.20 | 0.20 |
| | | Malic acid (*16) | 0.01 | 0.01 | 0.01 | 0.01 | 0.01 |
| | | Sodium hydroxide | Amount that makes pH 6 | Amount that makes pH 9.5 | | | |
| | | Fragrance | Moderate | | | | |
| | | Purified water | Balance | | | | |
| | | Total | 100 | 100 | 100 | 100 | 100 |
| | | pH | 6 | 9.5 | 9.5 | 9.5 | 9.5 |
| | | Mass ratio (A)/(B) | 0.25 | 0.25 | 0.22 | 0.25 | 0.27 |
| | | Mass ratio (A)/(C) | 1.00 | 1.00 | 1.00 | 1.00 | 1.00 |
| | | Mass ratio (A)/(D) | 1.00 | 1.00 | 1.00 | 1.00 | 1.00 |
| | | Mass ratio (D)/(C) | 1.00 | 1.00 | 1.00 | 1.00 | 1.00 |
| Evaluation | | Shape fixing ability of hair Bundle width (cm) | 0.70 | 0.60 | 0.80 | 1.10 | 0.70 |
| | | Shape fixing ability of hair Δ Length (cm) | 0.6 | 0.0 | 0.0 | −0.5 | 0.0 |

Annotations of *1 to *16 in Table 4 are shown below. In addition, % by mass in Table 4 is the amount of active ingredients.
*1 Carbopol 980 manufactured by Lubrizol Co., Ltd.
*2 EMAL 170S-A (70% by mass of active ingredient) manufactured by Kao Corporation
*3 EMAL 125HP (25% by mass of active ingredient) manufactured by Kao Corporation
*4 EMAL 227HP (27% by mass of active ingredient) manufactured by Kao Corporation
*5 Production example 1
*6 Bio-Terge AS-40 (40% by mass of active ingredient) manufactured by STEPAN COMPANY,
*7 SoftCAT SL-100 manufactured by Dow Chemical Company
*8 OFCARE KG-101W-E (2.4% by mass of active ingredient) manufactured by Kao Corporation,
*9 MPHITOL 20AB (30% by mass of active ingredient) manufactured by Kao Corporation
*10 18-MEA manufactured by Croda International Plc
*11 FARMIN DM E-80 manufactured by Kao Corporation (90% by mass of active ingredient)
*12 Benzyl alcohol manufactured by Toyotama International Inc.
*13 Hisolve EPH manufactured by Toho Chemical Industry Co., Ltd.
*14 DOWSIL Silstyle 201 manufactured by Dow Toray Industries, Inc.
*15 ABIL QUAT 3272 manufactured by Evonik Industries AG
*16 DL-malic acid manufactured by FUJIFILM Wako Pure Chemical Corporation

[Measurement Method of Various Physical Properties]

(i) Measurement Method of the Double Bond Position of the Raw Material Olefin

The double bond position of the raw material olefin was measured by gas chromatography (hereinafter abbreviated as GC). Specifically, the raw material olefin was reacted with dimethyl disulfide to obtain a dithio derivative, and then each component was separated by GC. As a result, the double bond position of the raw material olefin was obtained from each peak area.

Note that, the equipment used for the measurement and analysis conditions are as follows. GC device (trade name: HP6890, manufactured by HEWLETT PACKARD), column (trade name: Ultra-Alloy-1HT capillary column 30 m×250 μm×0.15 μm, manufactured by Frontier Laboratories Ltd.), detector (hydrogen flame ion detector (FID)), injection temperature 300 °C, detector temperature 350 °C, He flow rate 4.6 mL/min.

(ii) Measuring Method of the Content According to the Sulfonic Acid Group Bonding Position of Sodium Internal Olefin Sulfonate Regarding the internal sodium olefin sulfonate to which the sulfonic acid group is bonded, the content of each internal sodium olefin sulfonate according to the sulfonic acid group bonding position was measured by high performance liquid chromatography/mass spectrometer (HPLC-MS). Specifically, the hydroxy forms to which the sulfonic acid groups are bound were separated by high performance liquid chromatography (HPLC), and each was identified by applying it to a mass spectrometer (MS). As a result, each content was determined from the HPLC-MS peak area.

Note that the equipment used for the measurement and conditions are as follows. HPLC device "LD20ASXR" (manufactured by Shimadzu Corporation), column "ODS Hypersil (registered trademark)" (4.6×250 mm, particle size: 3 μm, manufactured by Thermo Fisher Scientific Inc.), sample preparation (1000 with methanol dilution), eluent A (10 mM ammonium acetate added water), eluent B (10 mM ammonium acetate added methacrylonitrile/water=95/5 (v/v) solution), gradient (0 min (A/B=60/40)→15.1 to 20 minutes (30/70)→20.1 to 30 minutes (60/40), MS instrument "LCMS-2020" (manufactured by Shimadzu Corporation), ESI detection (anion detection m/z: 321.10 ((A) component with 16 or 18 carbon atoms), column temperature (40 °C), flow rate (0.5 mL/min), injection volume (5 μL).

(iii) Measurement Method of the Mass Ratio of Hydroxy Form/Olefin Form

The mass ratio of the hydroxy form/olefin form of sodium internal olefin sulfonate was measured by HPLC-MS. Specifically, the hydroxy form and the olefin form were separated by HPLC and identified by subjecting them to MS. As a result, each ratio was obtained from the HPLC-MS peak area.

The equipment used for the measurement and conditions are as follows. HPLC device (trade name: Agilent Technologies 1100, manufactured by Agilent Technologies), column (trade name: L-column ODS 4.6×150 mm, manufactured by Chemicals Evaluation and Research Institute), sample preparation (1000-fold dilution with methanol), eluent A (10 mM ammonium acetate added water), eluent B (10 mM ammonium acetate added methanol), gradient (0 min (A/B=30/70%)→10 min (30/70%)→55 min (0/100%)→65 minutes (0/100%)→66 minutes (30/70%)→75 minutes (30/70%)), MS equipment (trade name: Agilent Technologies 1100MS SL (G1946D)), MS Detection (anion detection m/z60-1600, UV240 nm).

(iv) Measurement Method of the Content of Raw Material Olefin

The content of the unreacted raw material olefin in the sodium internal olefin sulfonate was measured by GC. Specifically, ethanol and petroleum ether were added to an aqueous solution of sodium internal olefin sulfonate, followed by extraction to obtain an olefin in the petroleum ether phase. As a result, the raw material olefin was quantified from the GC peak area.

The equipment used for the measurement and analysis conditions are as follows. GC device (trade name: Agilent Technologies 6850, manufactured by Agilent Technologies), column (trade name: Ultra-Alloy-1HT capillary column 15 m×250 μm×0.15 μm, manufactured by Frontier Laboratories Ltd.), detector (flame ion detection device (FID)), injection temperature 300 °C, detector temperature 350 °C, He flow rate 3.8 mL/min.

(v) Measurement Method of the Content of Inorganic Compounds

The content of inorganic compounds was measured by potentiometric titration and neutralization titration. Specifically, the content of $Na_2SO_4$ was quantified by determining the sulfate radical ($SO_4^{2-}$) by potentiometric titration. In addition, the content of NaOH was quantified by neutralization titration with dilute hydrochloric acid.

Production Example 1

[Production of Sodium Internal Olefin Sulfonate (DBP: 4.2)]

In a flask equipped with a stirrer, 7000 g (28.9 mol) of 1-hexadecanol (product name: KALCOL 6098, manufactured by Kao Corporation) and 350 g of γ-alumina (manufactured by STREM Chemicals, Inc.) as a solid acid catalyst (5% by mass relative to raw material alcohol) were added, and the reaction was carried out for 8 hours under stirring at 280 °C while circulating nitrogen (7000 mL/min) in the system. The alcohol conversion rate after completion of the reaction was 100%. The obtained crude alkene internal olefin was transferred to a distillation flask and distilled at 136 to 160 °C/4.0 mmHg to obtain a raw material olefin a1 having 16 carbon atoms and the olefin purity of 100%. The double bond distribution of the obtained raw material olefin a1 was 1.8% by mass at C1-position, 21.8% by mass at C2-position, 18.7% by mass at C3-position, 18.6% by mass at C4-position, and 14.3% by mass at C5-position, 11.4% by mass at C6-position, 13.6% by mass in total at C7 and 8-positions, and the average double bond position was 4.17.

The obtained raw material olefin was placed in a thin film sulfonation reactor having an external jacket, and the sulfonation reaction was carried out using sulfur trioxide gas under the condition that cooling water of 10 °C was passed through the outer jacket of the reactor. The $SO_3$/internal olefin molar ratio during the sulfonation reaction was set to 1.01. The resulting sulfonated product was mixed with an alkaline aqueous solution prepared with 1.04 moles of sodium hydroxide (alkaline agent) relative to the theoretical acid value, and neutralized at 30 °C for 1 hour by a continuous method. The resulting neutralized product was hydrolyzed by heating in an autoclave at 170 °C for 1 hour to obtain sodium internal olefin sulfonate 1 having 16 carbon atoms. The content of raw material olefin contained in the obtained sodium internal olefin sulfonate 1 having 16 carbon atoms was 0.4% by mass, and the content of inorganic compounds was 0.39% by mass.

Production Example 2

[Production of Sodium Internal Olefin Sulfonate (DBP: 3.6)]

A raw material olefin a2 having 16 carbon atoms and an olefin purity of 100% was obtained in the same manner as in Production Example 1, except that the reaction time was changed to 6 hours. The double bond distribution of the obtained raw material olefin a2 was 2.4% by mass at C1-position, 31.8% by mass at C2-position, 23.7% by mass at C3-position, 16.9% by mass at C4-position, 10.3% by mass at C5-position, 7.1% by mass at C6-position, and 7.9% by mass in total at C7 and C8-positions, and the average double bond position was 3.58.

Sodium internal olefin sulfonate 2 having 16 carbon atoms was obtained in the same manner as in Production Example 1, except that the obtained raw material olefin a2 was used. The content of raw material olefin contained in the obtained sodium internal olefin sulfonate 2 having 16 carbon atoms was 0.4% by mass, and the content of inorganic compounds was 0.42% by mass.

From Tables 1 to 4, in the evaluation of the shape fixing ability of the hair bundle, the hair cosmetics of the present examples had small bundle width and Δ length, and the shape fixing ability of the hair bundle was improved. That is, it can be understood that according to the hair cosmetic of the present invention, it is possible to improve the shape fixing ability for fixing the shape of the bundled hair while imparting a certain shape by bundling the hair, and particularly, to fix the peculiar hair such as curly hair, into a straight shape by bundling.

INDUSTRIAL APPLICABILITY

By the present invention, it is possible to provide the hair cosmetic which improved the shape fixing ability of the hair.

The invention claimed is:

1. A hair cosmetic comprising the following components (A) to (D):

(A) an anionic polymer;

(B) an anionic surfactant;

(C) a cationic polymer having a cellulose backbone; and (D) a cross-linked cationic vinyl polymer, wherein the mass ratio ((A)/(B) of the component (A) to the component (B) is 0.03 to 3.0, and the mass ratio ((D)/(C)) of the component (D) to the component (C) is 0.10 to 3.0.

2. The hair cosmetic according to claim 1, wherein, the component (D) comprises a cross-linked cationic vinyl polymer obtained by copolymerizing the following monomers (d1) to (d3):

(d1) at least one selected from monomers represented by the following formula (1);

(1)

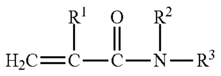

wherein, $R^1$ represents a hydrogen atom or a methyl group; $R^2$ represents a hydrogen atom, a linear or branched alkyl group or alkenyl group having 1 or more and 4 or less carbon atoms; and $R^3$ represents a linear or branched alkyl group or alkenyl group having 1 or more and 4 or less carbon atoms, (d2) at least one selected from monomers represented by the following formula (2);

(2)

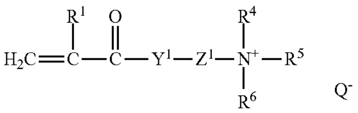

wherein, $R^1$ represents a hydrogen atom or a methyl group; $R^4$ and $R^5$ each independently represent an alkyl group or an alkenyl group having 1 or more and 4 or less carbon atoms; and $R^6$ is a hydrogen atom or an alkyl group having 1 or more and 4 or less carbon atoms; $Y^1$ is —O—, —NH—, —$CH_2$—or—O—$CH_2CH$ (OH)-group; and when $Y^1$ is-$CH_2$-, $Z^1$ represents a single bond or a linear or branched divalent saturated hydrocarbon group having 1 or more and 3 or less carbon atoms, and when $Y^1$ is other than —$CH_2$—, $Z^1$ represents a linear or branched divalent saturated hydrocarbon group having 1 or more and 4 or less carbon atoms; and Q represents a conjugate base of the acid, and (d3) a cross-linkable monomer having two or more reactive unsaturated groups.

3. The hair cosmetic according to claim 1, wherein the component (D) comprises a copolymer of N,N-dimethylaminoethyl methacrylate diethyl sulfate/N,N-dimethylacrylamide/(poly) ethylene glycol dimethacrylate.

4. The hair cosmetic according to claim 1, wherein the component (C) comprises a hydrophobic cationized hydroxyethyl cellulose.

5. The hair cosmetic according to claim 1, wherein a mass ratio ((D)/(C)) of the component (D) with respect to the component (C) is 0.20 or more and 2.5 or less.

6. The hair cosmetic according to claim 1, wherein the component (A) comprises at least one selected from a cross-linked polyacrylic acid and an (acrylates/alkyl acrylate (C10-30)) cross polymer.

7. The hair cosmetic according to claim 1, wherein a content of the component (A) is 0.01% by mass or more and 5.0% by mass or less.

8. The hair cosmetic according to claim 1, wherein a content of the component (B) is 0.1% by mass or more and 20% by mass or less.

9. The hair cosmetic according to claim 1, wherein a content of the component (C) is 0.01% by mass or more and 5.0% by mass or less.

10. The hair cosmetic according to claim 1, wherein a content of the component (D) is 0.01% by mass or more and 5.0% by mass or less.

11. A hair treatment method comprising:

applying the hair cosmetic according to claim 1 to a hair; and rinsing the hair in which the hair cosmetic is applied, with water.

12. The hair cosmetic according to claim 1, wherein the component (B) comprises at least one selected from polyoxyethylene alkyl ether sulfate, alkyl benzene sulfonate, a-olefin sulfonate, internal olefin sulfonate, alkyl or alkenyl sulfate, alkyl sulfonate, saturated or unsaturated fatty acid salt, alkyl or alkenyl ether carboxylic acid salts, a-sulfo fatty acid salts, N-acylamino acid salts, phosphoric acid mono-or diester salts, and sulfosuccinic acid ester salts.

13. The hair cosmetic according to claim 1, wherein a mass ratio ((A)/(D)) of the component (A) with respect to the component (D) is 0.10 or more and 12 or less.

14. The hair cosmetic according to claim 1, wherein a mass ratio ((A)/(C)) of the component (A) with respect to the component (C) is 0.10 or more and 12 or less.

15. The hair cosmetic according to claim 1, wherein a total content of the components (A) to (D) is 0.5% by mass or more and 25% by mass or less.

16. The hair cosmetic according to claim 1, wherein a pH of the hair cosmetic is 3.0 or more and 12.0 or less.

17. The hair cosmetic according to claim 1, further comprising an aqueous medium.

18. The hair cosmetic according to claim 17, wherein the aqueous medium further comprises at least one selected from ethanol, isopropyl alcohol, 1,3-butylene glycol, glycerin, ethylene glycol, propylene glycol, and dipropylene glycol.

19. The hair cosmetic according to claim 17, wherein a content of the aqueous medium is 60% by mass or more and 99% by mass or less.

20. The hair cosmetic according to claim 1, which is liquid, foam, paste or cream.

* * * * *